United States Patent
Alsters et al.

(10) Patent No.: US 9,035,078 B2
(45) Date of Patent: May 19, 2015

(54) PREPARATION OF NITRILE COMPOUNDS

(75) Inventors: Paulus Lambertus Alsters, Geleen (NL); Edwin Gerard Ijpeij, Geleen (NL)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 14/131,344

(22) PCT Filed: Jul. 6, 2012

(86) PCT No.: PCT/EP2012/063254
§ 371 (c)(1),
(2), (4) Date: Apr. 4, 2014

(87) PCT Pub. No.: WO2013/007634
PCT Pub. Date: Jan. 17, 2013

(65) Prior Publication Data
US 2014/0213804 A1    Jul. 31, 2014

(30) Foreign Application Priority Data
Jul. 8, 2011 (EP) ..................... 11173301

(51) Int. Cl.
| C07D 301/03 | (2006.01) |
| C07D 303/08 | (2006.01) |
| C07C 255/16 | (2006.01) |
| C07D 301/12 | (2006.01) |
| C07D 303/38 | (2006.01) |
| C07C 253/30 | (2006.01) |
| C07D 303/46 | (2006.01) |

(52) U.S. Cl.
CPC ............ *C07C 255/16* (2013.01); *C07D 301/12* (2013.01); *C07D 303/38* (2013.01); *C07C 253/30* (2013.01); *C07D 303/46* (2013.01)

(58) Field of Classification Search
USPC ................................... 549/523, 551; 558/451
See application file for complete search history.

(56) References Cited

U.S. PATENT DOCUMENTS
2,468,436 A    4/1949   Fitzpatrick et al.
6,770,679 B1 *  8/2004   Sandberg ...................... 516/203

FOREIGN PATENT DOCUMENTS
WO    WO 01/00605      1/2001
WO    WO 2006/118923   11/2006
WO    WO 2010/089512   8/2010

OTHER PUBLICATIONS

International Serarch Report for PCT/EP2012/063254, mailed Aug. 2, 2012.
Alami, E., "Heterogemini Surfactants Based on Fatty Acid Synthesis and Interfacial Properties", Journal of Colloid and Interface Science, vol. 239, No. 1, (Jul. 1, 2001), pp. 230-240.
Wrigley, A.N. et al., "The oxyethylation of 9,10-octdecanediols and 9,10-dihydroxystearonitrile. Nonionic soaps", Journal of the American Oil Chemists' Society, vol. 39, (Jan. 1, 1962), pp. 80-84.

* cited by examiner

*Primary Examiner* — T. Victor Oh
(74) *Attorney, Agent, or Firm* — Nixon & Vanderhye P.C.

(57) ABSTRACT

The invention relates to novel nitrile compounds according to formula I and II: (I) Formula I wherein: X=—CH₃ or —C≡N, (II) Formula II wherein: X=—CH₃ or —C≡N, each Y is independently chosen from —OH or RC(O)0-, each R is independently chosen from a C1-21 alkyl group. The invention also relates to processes for the preparation of nitrile compounds according to formula I and II and to uses of the nitrile compounds.

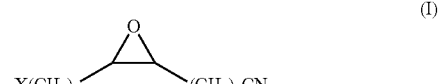

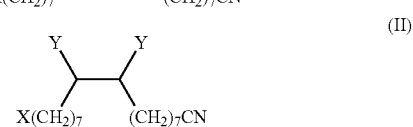

12 Claims, No Drawings

PREPARATION OF NITRILE COMPOUNDS

This application is the U.S. national phase of International Application No. PCT/EP2012/063254, filed 6 Jul. 2012, which designated the U.S. and claims priority to EP Application No 11173301.0, filed 8 Jul. 2011, the entire contents of each of which are hereby incorporated by reference.

The invention relates to the preparation of nitrile compounds starting from oleic acid. The invention also relates to the compounds as such and to novel intermediates and to the use of the novel intermediates, for example in the preparation of polymers, especially polyamides.

C18-based natural compounds, such as for example oleic acid are sometimes used to prepare a variety of shorter chain compounds with a nitrogen-functionality incorporated, such as for example amino-acids. A possible route to these nitrogen-functional short chain compounds is via the formation of an unsaturated nitrile of the same carbon length as the starting compound. If the starting compound is an unsaturated mono-acid (such as for example oleic acid), an unsaturated mono-nitrile of the same carbon length can be obtained. However when the starting compound is an unsaturated di-acid, an unsaturated di-nitrile can be obtained. The unsaturated di-acid with the same carbon length can be obtained from the unsaturated mono-acid by fermentative oxidation as described in for example WO2010/089512 and the references therein. An unsaturated di-acid with a similar or different chain length than the starting mono-acid can for example be obtained from the unsaturated mono-acid by metathesis. This technique is well-known to the man skilled in the art and is also described in, for example, WO2010/089512 and the references therein.

Oleic acid (or cis-octadec-9-enoic acid) is often used as a starting compound as it is a renewable, or bio-based, source of carbon. This makes processes that use oleic acid advantageous over processes that are based on oil-based sources of carbon as the amount of oil-based carbon sources is finite and its use reduces the net carbon dioxide emission by these processes.

The incorporation of a nitrogen functionality into an unsaturated fatty acid of natural source is described in WO2010/089512. Here it is described how oleic acid is converted into an amino-acid. Oleic acid is first fermented to give the corresponding 1,18-diacid (i.e. octadec-9-enedinitrile), which in turn is converted into the dinitrile by contacting the diacid with ammonia. The dinitrile is oxidatively cleaved into the smaller 8-cyanooctanoic acid (with half of the number of carbon atoms compared to oleic acid). From here the nitrile group is converted into an amine group by the action of hydrogen in a catalyzed reaction step to generate 9-amino nonanoic acid.

A disadvantage of this route to convert oleic acid into 9-amino nonanoic acid is that ozone is used to oxidatively cleave the double bond in oleic di-nitrile (1,18-dinitrile). The use of ozone makes the process expensive. It is mentioned that hydrogen peroxide can be used for the oxidation of the double bond as described in GB743491. However GB743491 describes the use of hydrogen peroxide for the oxidation of the double bond in oleic acid under acidic conditions. This reference doesn't teach how a double bond in an unsaturated di-nitrile can be oxidized while retaining nitrile-functionalities. It is known that nitrile groups are susceptible to hydrolysis especially in the presence of aqueous hydrogen peroxide, notably under basic conditions, but also under acidic conditions. Thus using hydrogen peroxide based oxidative cleavage methods for unsaturated oleic acid derived C18 nitriles, faces the risk of (partially) losing the nitrogen functionality, which is not acceptable even when only occurring to a slight extent when the ultimate product formed by oxidative cleavage is to be used as an amino-functionalized monomer for polymers.

It is therefore an object of the invention to overcome or at least reduce these disadvantages. Further it is an object of the invention to make available a process for the production of a nitrile compound according to formula I:

Formula I wherein
X is —CH₃ or —C≡N.

It has now been found that the nitrile compound according to formula I can be prepared and that the disadvantages can be solved, or at least diminished, by a process for the preparation of a nitrile compound according to formula I, that comprises at least the step of contacting octadec-9-enenitrile or octadec-9-enedinitrile with hydrogen peroxide under suitable conditions to oxidize the double bond without leading to oxidative carbon-carbon double bond cleavage to generate the corresponding C18-nitrile derivatives according to formula I. The compounds according to formula I thus contain an oxygenated functionality on C9 and C10. This process step is preferably performed in the presence of an epoxidation catalyst.

An important advantage of this process is that it makes available a completely new category of compounds, namely compounds according to formula I:

Formula I wherein
X is —CH₃ or —C≡N.

Both the like- and unlike-diastereomers can be obtained. Thus, according to one embodiment, the invention relates to the like diastereomer of the nitrile compound of formula I. According to another embodiment, the invention relates to the unlike diastereomer of the nitrile compound of formula I. It is also possible to obtain a racemic mixture comprising both enantiomers of the nitrile compound of formula I.

Preferably in the compound of formula I X is —C≡N.

These oleic acid derived C18 nitriles in which the double bond is partially oxidized without leading to carbon-carbon cleavage, are important intermediates in the process towards the production of 9-amino nonanoic acid as a monomer obtained from 8-cyanooctanoic acid. Further these compounds can be used as intermediates for oxy-functionalized 1,18-diamine C18 monomers (obtained by hydrogenation of the nitrile groups) or e.g. as (intermediate for) surfactants or lubricants. Via epoxide-ring opening polymerization technologies, these compounds can also serve as a monomer as such, either in a homopolymerization process, or in a copolymerization process, e.g. with carbon dioxide to generate nitrile-functionalized polycarbonates.

It is a further object of the invention to make available a process for the production of a nitrile compound according to formula II:

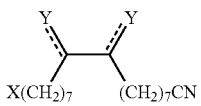

Formula II wherein:
X is —CH$_3$ or —C≡N,
each Y is independently chosen from =O, —OH, —OOH or RCOO—,
each R is independently chosen from a C1-21 alkyl group.
In the above formula

stands for a substituent Y that is bound to the adjacent C atom by either a single or double bond. This depends on the nature of substituent Y.

It has now been found that the nitrile compound according to formula II can be prepared and that the disadvantages can be solved, or at least diminished, by a process for the preparation of a nitrile compound according to formula II, that comprises at least the following steps:
contacting octadec-9-enenitrile or octadec-9-enedinitrile with hydrogen peroxide under suitable conditions to oxidize the double bond without leading to oxidative carbon-carbon double bond cleavage to generate the corresponding C18-nitrile derivatives according to formula I,
contacting the C18 nitrile oxidation product of the first step with water, hydrogen peroxide and/or a carboxylic acid RC(O)OH (with R being an alkyl group with 1-21 carbon atoms) under conditions to generate the nitrile compound according to formula II.

Preferably, a Brønsted acid or a Lewis acid, or metal catalyst is present in the second step to catalyze generation of the nitrile compound according to formula II. A combination of these catalysts may also be used. The first step and second step may also be carried out consecutively in the same reaction medium and under the same condition.

An additional advantage of the process for the production of oleic acid derivatives according to Formula II as described here, is that it makes available a category of novel compounds according to formula II:

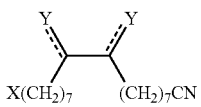

Formula II wherein:
X is —CH$_3$ or —C≡N,
each Y is independently chosen from =O, —OH, —OOH and RC(O)O—,
each R is independently chosen from a C1-21 alkyl group.
Both the like- and unlike-diastereomers can be obtained. Thus, according to one embodiment, the invention relates to the like diastereomer of the compound of formula II. According to another embodiment, the invention relates to the unlike diastereomer of the compound of formula II. It is also possible to obtain a racemic mixture comprising both enantiomers of the compound of formula II.

Preferably each Y is independently chosen from OH and RC(O)O—.

Preferably each R is independently chosen from a C1-C5 alkyl group, more preferably a C1-C3 alkyl group, most preferably each R is CH$_3$. The alkyl group can be linear or branched, but a linear group is preferred.

Preferably in a nitrile compound of formula II, X is —CH$_3$, and either both Y are RC(O)O— or one Y is —OH and one Y is RCO(O)—. Thus, when X is —CH$_3$ not both Y groups are —OH at the same time.

Preferred compounds according to formula II are those where both Y are chosen to be the same such as for example both Y are —OH or both Y are RC(O)O— with R being methyl. Another preferred class of compounds according to formula II are those compounds wherein both Y are different, such as for example with one Y being OH and the other Y being RC(O)O— with R being methyl.

These compounds can be used as intermediates for oxy-functionalized 1,18-diamine C18 monomers (obtained by hydrogenation of the nitrile groups) or e.g. as (intermediate for) surfactants or lubricants.

An advantageous class of compounds that has now become available are those compounds according to formula's I or II wherein X is chosen to be —C≡N, because in this case a di-nitrile is formed. These di-nitrile compounds are highly relevant as intermediates towards 8-cyano-octanoic acid, as it can be formed according to this invention from octadec-9-enedinitrile via oxidation with hydrogen peroxide and thus constitute intermediates in a 100% carbon-efficient route towards 8-cyanooctanoic acid.

Another advantageous class of compounds that has now become available is the class of compounds according to formula I or II wherein X is chosen to be —CH$_3$, thus generating mono-nitriles.

The compound according to formula II can now be turned into 8-cyanooctanoic acid by a process comprising at least the following step of contacting the compound according to formula II with hydrogen peroxide or dioxygen under suitable conditions for oxidatively cleaving the C9-C10 carbon-carbon bond.

An advantage of this process for the preparation of 8-cyanooctanoic acid is that it is much more economical than prior art processes. Further the overall process is highly carbon-efficient when based on octadec-9-enedinitrile, that on oxidative cleavage generates 2 equivalents of 8-cyanooctanoic acid. With carbon-efficiency is meant the percentage of carbon atoms from the starting material, here oleic acid, that is used for forming the product. The process is particularly cost-efficient with respect to the overall oxidant costs related to the oxidative cleavage when this is done with dioxygen.

In terms of process simplicity, the process is based on a particularly simple process design when the first step is carried out in a medium that is compatible with the second step, so that the medium containing the C18 nitrile oxidation product obtained in the first step can be used without intermediate product isolation for carrying out the second oxidative cleavage step. An example of such a medium is acetic acid, in which under the influence of a strong acid catalyst C18-nitrile derivatives according to formula I can be generated from octadec-9-enenitrile or octadec-9-enedinitrile with hydrogen peroxide via in situ formation of peracetic acid as epoxidizing agent. The C18-nitrile derivatives according to formula I react with water, hydrogen peroxide, and/or acetic acid to generate the nitrile compound according to formula II.

Combined advantages related to low oxidant cost and simple process design are particularly evident when the first step is done under acid catalysis without metal catalyst, in a solvent-containing medium that is compatible with the second step, which in turn is based on metal-catalyzed oxidative cleavage with dioxygen. In that case, the metal catalyst and dioxygen can be fed directly into the C18 nitrile oxidation product containing medium obtained in the first step without intermediate product isolation, and no costly step is required for separation of more than one metal catalyst.

8-Cyanooctanoic acid can be converted into 9-amino nonanoic acid. The nitrile-group in 8-cyanooctanoic acid can be hydrogenated through methods well-known to the man skilled in the art upon which the amine-containing 9-amino nonanoic acid is formed. 9-Amino nonanoic acid can be used, amongst others, in the production of polymers such as for example polyamides.

The present invention is further explained in the following examples without being limited to them.

EXPERIMENTAL

The preparation of several of the compounds described above in a general manner is given below.

Example 1

Preparation of like-8,8'-(oxirane-2,3-diyl)dioctanenitrile

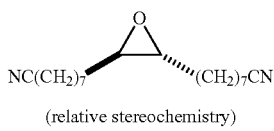

(relative stereochemistry)

A mixture of 0.1000 g (E)-octadec-9-enedinitrile and 0.2334 g NaHCO$_3$ in 4.0 mL acetone was cooled in an ice water bath. While stirring, a solution of 0.5365 g Oxone® in 4.0 mL water was added in portions during 30 min. The mixture was allowed to warm to room temperature over 18 h, then 200 mL CH$_2$Cl$_2$ and 10 mL water were added to the reaction mixture to afford a clear 2-phase system. The organic phase was dried over Na$_2$SO$_4$ and evaporated to afford 0.10 g of product as a colorless oil.

Selected $^1$H NMR data (300 MHz, CDCl$_3$): δ 2.56 (m, 2H, CH), 2.26 (t, 4H, CH$_2$), 1.57 (q, 4H, CH$_2$). Selected $^{13}$C NMR data (75 MHz, CDCl$_3$): δ 119.66, 58.50.

Example 2

Preparation of unlike-8,8'-(oxirane-2,3-diyl)dioctanenitrile

This product was prepared using the same procedure as in Example 1, except that (Z)-octadec-9-enedinitrile was used instead of (E)-octadec-9-enedinitrile.

Example 3

Preparation of unlike-9,10-dihydroxyoctadecanedinitrile

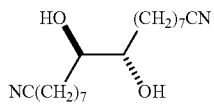

To a solution of 0.10 g like-8,8'-(oxirane-2,3-diyl)dioctanenitrile in 5.0 g THF was added 0.50 mL of a solution of 0.0988 g 70% HClO$_4$ in 1.9104 g water. After standing for 24 h at room temperature, the mixture was diluted with 250 mL CH$_2$Cl$_2$, which resulted in the separation of aqueous droplets. The mixture was dried over Na$_2$CO$_3$ and evaporated to afford 0.10 g of product as a white powder.

Selected $^1$H NMR data (300 MHz, CDCl$_3$): δ 3.57 (m, 2H, CH), 2.33 (t, 4H, CH$_2$), 1.65 (q, 4H, CH$_2$). Selected $^{13}$C NMR data (75 MHz, CDCl$_3$): δ 119.91, 74.66.

Example 4

Preparation of like-9,10-dihydroxyoctadecanedinitrile

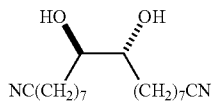

(relative stereochemistry)

This product was prepared using the same procedure as in Example 3, except that unlike-8,8'-(oxirane-2,3-diyl)dioctanenitrile was used instead of like-8,8'-(oxirane-2,3-diyl)dioctanenitrile.

Example 5

Preparation of unlike-1,16-dicyano-9-hydroxyhexadecan-8-ylacetate

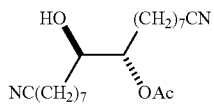

(relative stereochemistry)

To a mixture of 0.10 g unlike-9,10-dihydroxyoctadecanedinitrile and 0.0013 g para-toluenesulfonic acid monohydrate in 2.5 mL dry CH$_2$Cl$_2$ was added 0.15 mL trimethyl orthoacetate. After stirring for 21 h at room temperature, volatiles were removed via a stream of nitrogen. To the residue was added a mixture of 0.20 mL water and 0.80 mL acetic acid, and the resulting solution was stirred for 150 min. To the mixture was added 25 mL MTBE, and the organic phase was extracted with 2×10 mL water, subsequently with 2×5 mL saturated aqueous NaHCO$_3$. The organic phase was dried over Na$_2$SO$_4$ and evaporated to afford 0.11 g of product as a slightly yellow very viscous oil.

Selected $^1$H NMR data (300 MHz, CDCl$_3$): δ 4.75 (m, 1H, CH), 3.58 (m, 1H, CH), 2.27 (t, 4H, CH$_2$), 2.01 (s, 3H, CH$_3$), 1.58 (m, 4H, CH$_2$). Selected $^{13}$C NMR data (75 MHz, CDCl$_3$): δ 171.10, 119.76, 77.41, 72.89.

Example 6

Preparation of like-1,16-dicyano-9-hydroxyhexadecan-8-ylacetate

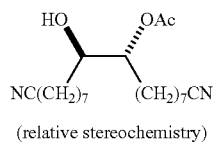

(relative stereochemistry)

This product was prepared using the same procedure as in Example 5, except that like-9,10-dihydroxyoctadecanedinitrile was used instead of unlike-9,10-dihydroxyoctadecanedinitrile.

Example 7

Preparation of unlike-1,16-dicyanohexadecane-8,9-diyldiacetate

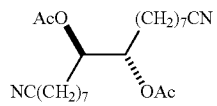

A mixture of 0.11 g unlike-1,16-dicyano-9-hydroxyhexadecan-8-yl acetate, 4.0 mL acetic anhydride (4.0 mL) and 0.24 g 4-(dimethylamino)pyridine in 25 mL dry pyridine was stirred for 3 h at room temperature. To the mixture was added 25 mL 8/2 heptane/ethyl acetate, and the organic phase was extracted with 3×25 mL saturated aqueous CuSO$_4$ to remove pyridine. The organic phase was dried over Na$_2$SO$_4$ and evaporated to afford 0.12 g of product.

Example 8

Preparation of like-1,16-dicyanohexadecane-8,9-diyldiacetate

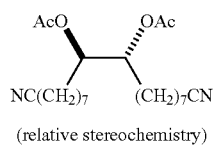

(relative stereochemistry)

This product was prepared using the same procedure as in Example 7, except that like-1,16-dicyano-9-hydroxyhexadecan-8-yl acetate was used instead of unlike-1,16-dicyano-9-hydroxyhexadecan-8-yl acetate.

Example 9

Preparation of a mixture of like-1-cyano-9-hydroxyheptadecan-8-yl acetate and like-1-cyano-8-hydroxyheptadecan-9-yl acetate

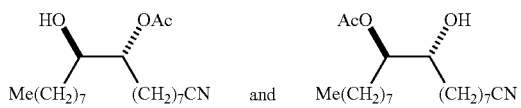

To a mixture of 0.38 g like-9,10-dihydroxyoctadecanenitrile and 0.0030 g para-toluenesulfonic acid monohydrate in 2.5 mL dry CH$_2$Cl$_2$ was added 0.50 mL trimethyl orthoacetate. After stirring for 21 h at room temperature, volatiles were removed via a stream of nitrogen. To the residue was added a mixture of 0.25 mL water and 1.05 mL acetic acid, and the resulting solution was stirred for 90 min. To the mixture was added 25 mL MTBE, and the organic phase was extracted with 2×10 mL water, subsequently with 2×5 mL saturated aqueous NaHCO$_3$. The organic phase was dried over Na$_2$SO$_4$ and evaporated to afford 0.42 g of product as a slightly yellow very viscous oil.

Selected $^1$H NMR data (300 MHz, CDCl$_3$): δ 4.68 (m, 1H, CH), 3.42 (m, 1H, CH), 2.20 (t, 2H, CH$_2$), 1.93 (s, 3H, CH$_3$), 1.49 (m, 4H, CH$_2$), 0.73 (t, 3H, CH$_3$). Selected $^{13}$C NMR data (75 MHz, CDCl$_3$): δ 170.68, 119.47, 76.37, 76.23, 71.87, 71.84.

Example 10

Preparation of a mixture of like-1-cyano-9-hydroxyheptadecan-8-yl acetate and like-1-cyano-8-hydroxyheptadecan-9-yl acetate via epoxidation of cis-octadec-9-enenitrile with in situ generated peracetic acid followed by epoxide opening

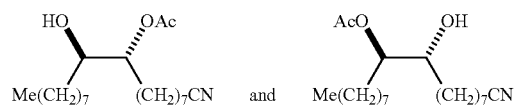

To a solution of 4.30 g cis-octadec-9-enenitrile in 100 mL acetic acid was added 100 μL 96% H$_2$SO$_4$. The mixture was heated to 100° C. and 0.93 mL 50% H$_2$O$_2$ was added in one portion. The mixture was stirred for 1 h. Although a peroxide test was negative, any non-detectable residual peroxide was destroyed by adding a small amount of aqueous Na$_2$SO$_3$ (10% solution). After removal of acetic acid and water by rotary evaporation, the residue was taken up in dichloromethane. The solution was dried on Na$_2$SO$_4$, filtered, and the filtrate was concentrated by rotary evaporation, leaving a waxy solid. This was shown to contain a mixture of like-1-cyano-9-hydroxyheptadecan-8-yl acetate and like-1-cyano-8-hydroxyheptadecan-9-yl acetate by $^1$H NMR. Quantitative $^{13}$C NMR on like-9,10-dihydroxyoctadecanenitrile obtained by mild saponification of this mixture (K$_2$CO$_3$ in methanol at room temperature) did not reveal nitrile hydrolysis, illustrating that the nitrile functionality of cis-octadec-9-enenitrile survives the acidic double bond oxidation conditions.

The invention claimed is:

1. A nitrile compound according to formula I:

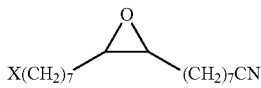

Formula I wherein X is —C≡N.

2. A nitrile compound according to formula II:

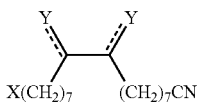

Formula II wherein:
X is —C≡N,
each Y is independently chosen from =O, —OH, —OOH and RC(O)O—, and
R is independently chosen from a C1-C21 alkyl group.

3. The nitrile compound according to claim 2, wherein each Y is independently chosen from —OH and RC(O)O—.

4. A nitrile compound according to formula II:

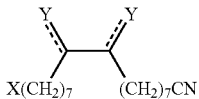

Formula II wherein X is —CH3, and either both Y are RC(O)O— or one Y is —OH and another Y is RCO(O)—, wherein R is independently chosen from a C1-C21 alkyl group.

5. The nitrile compound according to claim 4, wherein R is independently chosen from a C1-C5 alkyl group.

6. The nitrile compound according to claim 5, wherein R is methyl.

7. A racemic mixture comprising both enantiomers of a nitrile compound according to claim 1.

8. A process for the preparation of a nitrile compound according to claim 1, wherein the process comprises at least the step of contacting octadec-9-enenitrile or octadec-9-enedinitrile with hydrogen peroxide under suitable conditions to oxidize the double bond without leading to oxidative carbon-carbon double bond cleavage.

9. A surfactant or lubricant which comprises the nitrile compound according to claim 1.

10. A process for the preparation of a nitrile compound according to formula II,

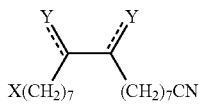

Formula II wherein:
X is —C≡N
each Y is independently chosen from =O, —OH, —OOH and RC(O)O—, and
R is independently chosen from a C1-C21 alkyl group, the process comprising at least the following steps:
(a) contacting octadec-9-enenitrile or octadec-9-enedinitrile with hydrogen peroxide under suitable conditions to oxidize the double bond without leading to oxidative carbon-carbon double bond cleavage to generate a corresponding C18-nitrile according to formula I,

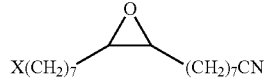

Formula I wherein X is as previously defined, and
(b) contacting the C18-nitrile according to formula I of step (a) with water, hydrogen peroxide and/or a carboxylic acid RC(O)OH, with R being as previously defined, under conditions to generate the nitrile compound according to formula II.

11. A surfactant or lubricant which comprises the nitrile compound according to claim 2.

12. A process for the preparation of 8-cyanooctanoic acid comprising at least the step of contacting the nitrile compound according to claim 2 with hydrogen peroxide or dioxygen under suitable conditions for oxidatively cleaving a C9-C10 carbon-carbon bond.

* * * * *